(12) United States Patent
Decarlo et al.

(10) Patent No.: US 9,848,932 B2
(45) Date of Patent: Dec. 26, 2017

(54) COOL-TIP THERMOCOUPLE INCLUDING TWO-PIECE HUB

(71) Applicant: COVIDIEN AG, Neuhausen am Rheinfall (CH)

(72) Inventors: Arnold V. Decarlo, Frederick, CO (US); Gene H. Arts, Berthoud, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 17 days.

(21) Appl. No.: 14/193,114

(22) Filed: Feb. 28, 2014

(65) Prior Publication Data

US 2014/0180279 A1    Jun. 26, 2014

Related U.S. Application Data

(60) Continuation of application No. 12/182,723, filed on Jul. 30, 2008, now Pat. No. 8,672,937, which is a
(Continued)

(51) Int. Cl.
*A61B 18/14*          (2006.01)
*A61B 18/00*          (2006.01)

(52) U.S. Cl.
CPC .......... *A61B 18/00* (2013.01); *A61B 18/1477* (2013.01); *A61B 2018/00023* (2013.01)

(58) Field of Classification Search
CPC  A61B 2018/00023; A61B 2018/00714; A61B 2018/0293; A61B 2018/00821; A61B 2018/1425
(Continued)

(56) References Cited

U.S. PATENT DOCUMENTS 2,031,682 A    2/1936    Wappler et al.
4,074,718 A    2/1978    Morrison, Jr.
(Continued)

FOREIGN PATENT DOCUMENTS

DE        2407559 A1    8/1975
DE    10224154 A1    12/2003
(Continued)

OTHER PUBLICATIONS

Cosman ER, Cosman BJ: "Methods of Making Nervous System Lesions", in William RH, Rengachary SS (eds): Neurosurgery. New York: McGraw-Hill, vol. 111, pp. 2490-2498, 1984.
(Continued)

*Primary Examiner* — Thomas Giuliani

(57) ABSTRACT

An ablation electrode system includes a handle assembly; a needle electrode assembly supported in and extending from the handle assembly. The needle electrode assembly includes an outer tube having at least a conductive distal tip and defining a cavity therein; and an inner tube disposed at least partially within the cavity of the outer tube and defining a lumen therein. The ablation electrode assembly includes a hub assembly fluidly connected to the needle electrode assembly. The hub assembly defines a first chamber and a second chamber; wherein the proximal end portion of the inner tube is in fluid communication with the first chamber and the proximal end portion of the outer tube is in fluid communication with the second chamber. The ablation electrode assembly includes a first fluid conduit fluidly connected to the first chamber; and a second fluid conduit fluidly connected to the second chamber.

14 Claims, 12 Drawing Sheets

Related U.S. Application Data division of application No. 11/495,033, filed on Jul. 28, 2006, now Pat. No. 7,763,018.

(58) Field of Classification Search
USPC .......................................... 606/44; 607/102
See application file for complete search history.

(56) References Cited

U.S. PATENT DOCUMENTS

| | | | |
|---|---|---|---|
| 4,375,220 A | 3/1983 | Matvias | |
| 4,411,266 A * | 10/1983 | Cosman | A61B 18/14 600/549 |
| 4,565,200 A | 1/1986 | Cosman | |
| 4,576,177 A | 3/1986 | Webster, Jr. | |
| 4,608,977 A | 9/1986 | Brown | |
| 4,662,383 A | 5/1987 | Sogawa et al. | |
| 4,739,759 A | 4/1988 | Rexroth et al. | |
| 4,832,024 A | 5/1989 | Boussignac et al. | |
| 4,880,719 A | 11/1989 | Murofushi et al. | |
| 4,961,435 A | 10/1990 | Kitagawa et al. | |
| 4,966,597 A | 10/1990 | Cosman | |
| 4,993,430 A | 2/1991 | Shimoyama et al. | |
| 5,029,588 A | 7/1991 | Yock et al. | |
| 5,103,804 A | 4/1992 | Abele et al. | |
| 5,225,741 A | 7/1993 | Auld, Jr. et al. | |
| 5,230,623 A | 7/1993 | Guthrie et al. | |
| 5,233,515 A | 8/1993 | Cosman | |
| 5,246,438 A | 9/1993 | Langberg | |
| 5,267,994 A | 12/1993 | Gentelia et al. | |
| 5,281,213 A | 1/1994 | Milder et al. | |
| 5,323,778 A | 6/1994 | Kandarpa et al. | |
| 5,330,470 A | 7/1994 | Hagen | |
| 5,330,518 A | 7/1994 | Neilson et al. | |
| 5,334,193 A | 8/1994 | Nardella | |
| 5,342,357 A | 8/1994 | Nardella | |
| 5,348,554 A | 9/1994 | Imran et al. | |
| 5,370,675 A | 12/1994 | Edwards et al. | |
| 5,383,876 A | 1/1995 | Nardella | |
| 5,383,917 A | 1/1995 | Desai et al. | |
| 5,385,148 A | 1/1995 | Lesh et al. | |
| 5,403,311 A | 4/1995 | Abele et al. | |
| 5,409,000 A | 4/1995 | Imran | |
| 5,409,006 A | 4/1995 | Buchholtz et al. | |
| 5,417,686 A | 5/1995 | Peterson et al. | |
| 5,433,739 A | 7/1995 | Sluijter et al. | |
| 5,437,662 A | 8/1995 | Nardella | |
| 5,458,597 A | 10/1995 | Edwards et al. | |
| 5,462,521 A | 10/1995 | Brucker et al. | |
| 5,472,441 A | 12/1995 | Edwards et al. | |
| 5,490,850 A | 2/1996 | Ellman et al. | |
| 5,500,012 A | 3/1996 | Brucker et al. | |
| 5,520,684 A | 5/1996 | Imran | |
| 5,536,267 A | 7/1996 | Edwards et al. | |
| 5,571,147 A | 11/1996 | Sluijter et al. | |
| 5,588,432 A | 12/1996 | Crowley | |
| 5,599,345 A | 2/1997 | Edwards et al. | |
| 5,643,197 A | 7/1997 | Brucker et al. | |
| 5,647,871 A | 7/1997 | Levine et al. | |
| 5,662,111 A | 9/1997 | Cosman | |
| 5,688,267 A | 11/1997 | Panescu et al. | |
| 5,735,847 A | 4/1998 | Gough et al. | |
| 5,775,338 A | 7/1998 | Hastings | |
| 5,792,146 A | 8/1998 | Cosman | |
| 5,848,967 A | 12/1998 | Cosman | |
| 5,849,011 A | 12/1998 | Jones et al. | |
| 5,868,740 A | 2/1999 | LeVeen et al. | |
| 5,921,982 A | 7/1999 | Lesh et al. | |
| 5,943,719 A | 8/1999 | Feldman et al. | |
| 5,951,546 A * | 9/1999 | Lorentzen | 606/41 |
| 6,001,093 A | 12/1999 | Swanson et al. | |
| 6,006,126 A | 12/1999 | Cosman | |
| 6,053,912 A | 4/2000 | Panescu et al. | |
| 6,059,780 A | 5/2000 | Gough et al. | |
| 6,061,551 A | 5/2000 | Sorrells et al. | |
| 6,074,389 A | 6/2000 | Levine et al. | |
| 6,080,149 A | 6/2000 | Huang et al. | |
| 6,106,524 A | 8/2000 | Eggers et al. | |
| 6,132,426 A | 10/2000 | Kroll | |
| 6,146,380 A | 11/2000 | Racz et al. | |
| 6,162,216 A | 12/2000 | Guziak et al. | |
| 6,183,263 B1 * | 2/2001 | Tacchi et al. | 439/8 |
| 6,203,541 B1 | 3/2001 | Keppel | |
| 6,241,725 B1 | 6/2001 | Cosman | |
| 6,246,912 B1 | 6/2001 | Sluijter et al. | |
| 6,273,882 B1 * | 8/2001 | Whittier | A61B 10/06 606/1 |
| 6,287,305 B1 | 9/2001 | Heim et al. | |
| 6,306,132 B1 | 10/2001 | Moorman et al. | |
| 6,337,998 B1 | 1/2002 | Behl et al. | |
| 6,432,070 B1 | 8/2002 | Talish et al. | |
| 6,478,793 B1 | 11/2002 | Cosman et al. | |
| 6,500,172 B1 | 12/2002 | Panescu et al. | |
| 6,506,189 B1 | 1/2003 | Rittman, III et al. | |
| 6,530,922 B2 | 3/2003 | Cosman et al. | |
| 6,575,969 B1 | 6/2003 | Rittman, III et al. | |
| 6,605,085 B1 | 8/2003 | Edwards | |
| 6,613,047 B2 | 9/2003 | Edwards | |
| 6,685,729 B2 | 2/2004 | Gonzalez | |
| 7,137,980 B2 | 11/2006 | Buysse et al. | |
| 7,156,842 B2 | 1/2007 | Sartor et al. | |
| 7,179,255 B2 | 2/2007 | Lettice et al. | |
| 7,186,222 B1 | 3/2007 | Callister et al. | |
| 7,207,989 B2 | 4/2007 | Pike, Jr. et al. | |
| 7,218,958 B2 | 5/2007 | Rashidi | |
| 7,235,070 B2 | 6/2007 | Vanney | |
| 7,235,073 B2 | 6/2007 | Levine et al. | |
| 7,238,184 B2 | 7/2007 | Megerman et al. | |
| 7,264,619 B2 | 9/2007 | Venturelli | |
| 7,278,991 B2 | 10/2007 | Morris et al. | |
| 7,282,049 B2 | 10/2007 | Orszulak et al. | |
| 7,294,127 B2 | 11/2007 | Leung et al. | |
| 7,294,143 B2 | 11/2007 | Francischelli | |
| 7,302,285 B2 | 11/2007 | Fuimaono et al. | |
| 7,303,558 B2 | 12/2007 | Swanson | |
| 7,331,947 B2 | 2/2008 | McGuckin, Jr. et al. | |
| RE40,156 E | 3/2008 | Sharps et al. | |
| 7,341,586 B2 | 3/2008 | Daniel et al. | |
| 7,344,533 B2 | 3/2008 | Pearson et al. | |
| 7,364,578 B2 | 4/2008 | Francischelli et al. | |
| 7,364,579 B2 | 4/2008 | Mulier et al. | |
| 7,367,974 B2 | 5/2008 | Haemmerich et al. | |
| 7,367,975 B2 | 5/2008 | Malecki et al. | |
| 7,387,625 B2 | 6/2008 | Hovda et al. | |
| 7,419,486 B2 | 9/2008 | Kampa | |
| 7,419,487 B2 | 9/2008 | Johnson et al. | |
| 7,419,488 B2 | 9/2008 | Ciarrocca et al. | |
| 7,419,489 B2 | 9/2008 | Vanney et al. | |
| 7,422,587 B2 | 9/2008 | Bek et al. | |
| 7,763,018 B2 * | 7/2010 | DeCarlo et al. | 606/41 |
| 8,672,937 B2 * | 3/2014 | DeCarlo et al. | 606/41 |
| 2001/0034518 A1 | 10/2001 | Edwards et al. | |
| 2002/0007180 A1 * | 1/2002 | Wittenberger | A61B 18/02 606/21 |
| 2002/0058933 A1 | 5/2002 | Christopherson et al. | |
| 2002/0111615 A1 | 8/2002 | Cosman et al. | |
| 2002/0120261 A1 | 8/2002 | Morris et al. | |
| 2002/0156472 A1 | 10/2002 | Lee et al. | |
| 2003/0018247 A1 | 1/2003 | Gonzalez | |
| 2003/0039453 A1 | 2/2003 | Holmquist et al. | |
| 2004/0002745 A1 | 1/2004 | Fleming et al. | |
| 2004/0039429 A1 | 2/2004 | Daniel et al. | |
| 2004/0059328 A1 | 3/2004 | Daniel et al. | |
| 2004/0181216 A1 | 9/2004 | Kelly et al. | |
| 2004/0199161 A1 | 10/2004 | Truckai et al. | |
| 2004/0254573 A1 | 12/2004 | Dycus et al. | |
| 2004/0267256 A1 | 12/2004 | Garabedian et al. | |
| 2005/0010200 A1 * | 1/2005 | Damasco | A61B 18/02 606/21 |
| 2005/0090818 A1 | 4/2005 | Pike et al. | |
| 2005/0096681 A1 | 5/2005 | Desinger et al. | |
| 2005/0107784 A1 | 5/2005 | Moses et al. | |
| 2005/0107785 A1 | 5/2005 | Dycus et al. | |
| 2005/0113824 A1 | 5/2005 | Sartor et al. | |
| 2005/0119655 A1 | 6/2005 | Moses et al. | |

(56) References Cited

U.S. PATENT DOCUMENTS

| | | |
|---|---|---|
| 2005/0154387 A1 | 7/2005 | Moses et al. |
| 2005/0155743 A1 | 7/2005 | Getz et al. |
| 2005/0192564 A1 | 9/2005 | Cosman et al. |
| 2005/0215946 A1* | 9/2005 | Hansmann ............. A61B 5/027 604/66 |
| 2006/0079885 A1 | 4/2006 | Rick et al. |
| 2006/0079886 A1 | 4/2006 | Orszulak et al. |
| 2006/0079887 A1 | 4/2006 | Buysse et al. |
| 2007/0066971 A1 | 3/2007 | Podhajsky |
| 2007/0073285 A1 | 3/2007 | Peterson |
| 2007/0078453 A1 | 4/2007 | Johnson et al. |
| 2007/0078454 A1 | 4/2007 | McPherson |
| 2007/0260240 A1 | 11/2007 | Rusin |
| 2008/0021448 A1 | 1/2008 | Orszulak et al. |
| 2008/0027424 A1 | 1/2008 | DeCarlo et al. |
| 2008/0077126 A1* | 3/2008 | Rashidi ............................ 606/34 |
| 2008/0183165 A1 | 7/2008 | Buysse et al. |

FOREIGN PATENT DOCUMENTS

| | | |
|---|---|---|
| EP | 171967 A2 | 2/1986 |
| EP | 0 246 350 A1 | 11/1987 |
| EP | 310431 A2 | 4/1989 |
| EP | 608609 A2 | 8/1994 |
| EP | 1 070 518 A2 | 1/2001 |
| EP | 1465037 A2 | 10/2004 |
| EP | 1 645 234 A1 | 4/2006 |
| EP | 1656900 A2 | 5/2006 |
| FR | 2 864 439 A1 | 7/2005 |
| WO | 93/24066 A1 | 12/1993 |
| WO | 94/28809 A1 | 12/1994 |
| WO | 96/04860 A1 | 2/1996 |
| WO | 96/18349 A2 | 6/1996 |
| WO | 96/29946 A1 | 10/1996 |
| WO | 96/34571 A1 | 11/1996 |
| WO | 96/39914 A1 | 12/1996 |
| WO | 97/06739 A2 | 2/1997 |
| WO | 97/06740 A2 | 2/1997 |
| WO | 97/06855 A2 | 2/1997 |
| WO | 97/17029 A1 | 5/1997 |
| WO | 9901074 A1 | 1/1999 |
| WO | 9904710 A1 | 2/1999 |
| WO | 9922657 A1 | 5/1999 |
| WO | 0067846 A1 | 11/2000 |
| WO | 0100114 A1 | 1/2001 |
| WO | 2004/045436 A1 | 6/2004 |
| WO | 2005009528 A1 | 2/2005 |

OTHER PUBLICATIONS

Anderson, Gary et al., "A numerical study of rapid heating for high temperature radio frequency hyperthermia", International Journal of Bio-Medical Computing, 35 (1994) 297-307.

Goldberg, et al., "Tissue Ablation with Radiofrequency: Effective Probe Size, Gauge, Duration and Temperature and Lesion Volume", Acad Radio, 1995, vol. 2, No. 5, pp. 399-404.

Melvin A. Astrahan, "A Localized Current Field Hyperthermia System for Use with 192-Iridium Interstitial Implants", Medical Physics, 9(3), May/Jun. 1982.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedence", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with Special Applicators for High-Frequency Interstitial Thermotherapy", Society Minimally Ivasive Therapy, 4(Suppl 1) :40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", Radiology, vol. 221, pp. 159-166.

Goldberg, et al., "Image-guided Radiofrequency Tumor Ablation: Challenges and Opportunities—Part I", (2001) J Vasc. Interv. Radiol, vol. 12, pp. 1021-1032.

McGahan et al. (1995) "Percutaneous Ultrasound-guided Radiofrequency Electrocautery Ablationof Prostate Tissue in Dogs", Acad Radiol, vol. 2, No. 1:pp. 61-65.

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

Bulletin of the American Physical Society, vol. 47, No. 5, Aug. 2002.

McRury, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.

European Search Report from Application EP 05021935 dated Jan. 27, 2006.

European Search Report from Application EP 05021939 dated Jan. 27, 2006.

European Search Report from Application EP 05021025 dated Mar. 13, 2006.

European Search Report from Application EP 05021936.9 dated Feb. 6, 2006.

European Search Report from Application EP 05025423.4 dated Jan. 12, 2007.

European Search Report from Application EP 06019768 dated Jan. 8, 2007.

European Search Report from Application EP 05025424 dated Jan. 23, 2007.

European Search Report from Application EP 07009028 dated Jul. 16, 2007.

Goldberg, et al., "Image-guided Radiofrequency Tumor Ablation: Challenges and Opportunities—Part 1", (2001 ) J Vasc. Interv. Radiol, vol. 12, pp. 1021-1032.

* cited by examiner

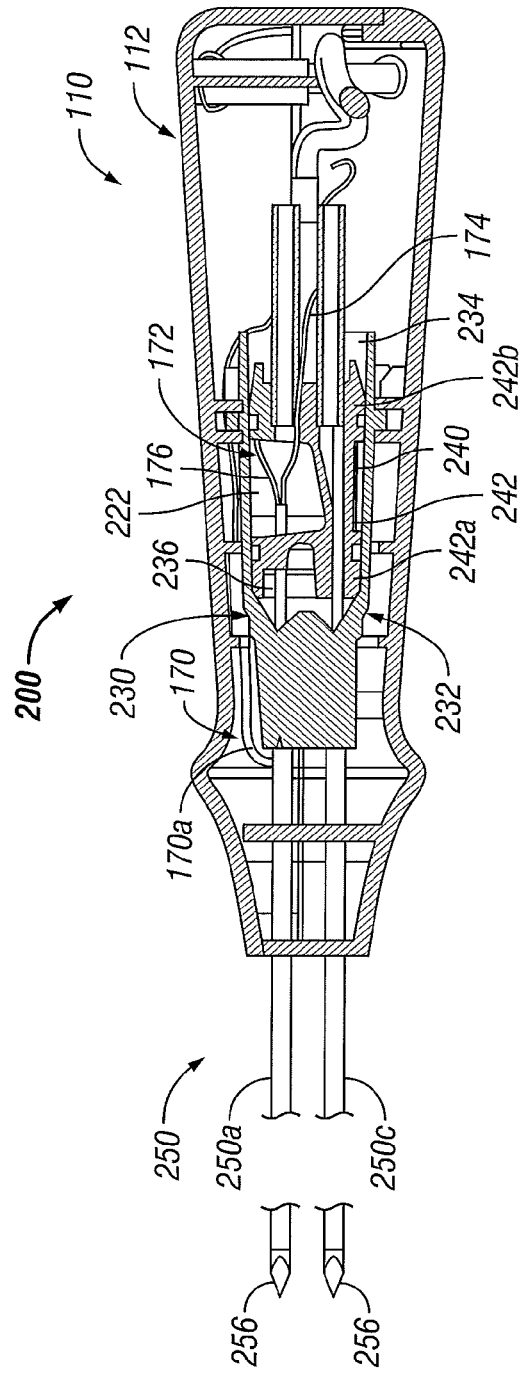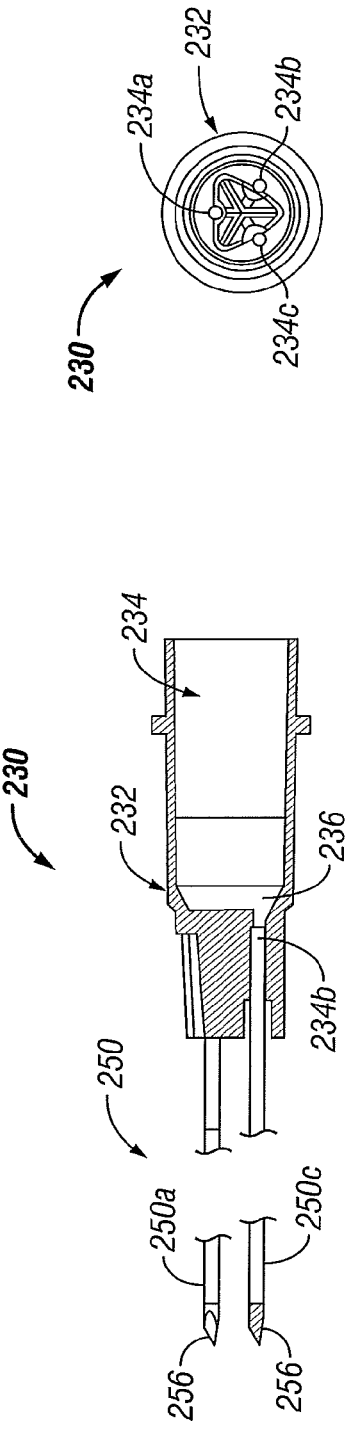
FIG. 9
FIG. 10
FIG. 10A

COOL-TIP THERMOCOUPLE INCLUDING TWO-PIECE HUB

CROSS-REFERENCE TO RELATED APPLICATION

The present application is a continuation application of U.S. application Ser. No. 12/182,723, filed Jul. 30, 2008, now U.S. Pat. No. 8,672,937, which is a divisional application of U.S. application Ser. No. 11/495,033, filed Jul. 28, 2006, now U.S. Pat. No. 7,763,018, the entire contents of all of which are incorporated by reference herein.

BACKGROUND

Technical Field

The present disclosure relates to electrode thermosurgery systems and, more particularly, to cool-tip ablation electrode systems used for thermosurgery procedures and the like.

Background of Related Art

Therapeutic lesions in living bodies have been accomplished for many decades using radio-frequency (RF) and other forms of energy. The procedures have been particularly useful in the field of neurosurgery, typically where RF ablation needle electrodes (usually of elongated cylindrical geometry) are inserted into a living body. A typical form of such needle electrodes incorporates an insulated sheath from which an exposed (uninsulated) tip extends.

Generally, the ablation electrode is coupled between a grounded RF power source (outside the body) and a reference ground or indifferent electrode for contacting a large surface of the body. When an RF voltage is provided between the reference electrode and the inserted ablation electrode, RF current flows from the needle electrode through the body. Typically, the current density is very high near the tip of the needle electrode, which heats and destroys the adjacent tissue.

In the past, RF ablation electrode systems have incorporated temperature sensors, for example, in the form of a thermistor or thermocouple. In that regard, reference may be made to U.S. Pat. No. 4,411,266 to Cosman, the entire contents of which are incorporated herein by reference, for a detailed discussion of the same. Typically, the sensor is connected to a monitoring apparatus for indicating temperature to assist in accomplishing a desired lesion. As generally known, for a given tip geometry and tip temperature, lesions of a prescribed size can be made quite consistently.

A limitation of prior electrode ablation systems relates to the temperature of the tip. Specifically, prior needle electrodes of a given tip geometry never should effectively exceed a temperature of 100° C. At that temperature, the surrounding tissue will boil and char. Also, uncontrolled disruption, such as hemorrhage and explosive gas formation, may cause extremely hazardous and clinically dangerous effects on the patient. Consequently, the lesion size for a given electrode geometry generally has been considered to be somewhat limited by the fact that the tissue near the tip must not exceed 100° C.

Essentially, during RF ablation, the needle electrode temperature is highest near the tip, because the current density is the highest at that location. Accordingly, temperature falls off as a function of distance from the tip of the needle electrode, and except for possible abnormalities in tissue conductivity and so on, in a somewhat predictable and even calculable pattern. As an attendant consequence, the size of RF lesions for a given electrode geometry have been somewhat limited.

One proposed solution to the limitation of lesion's size has been to employ "off-axis" electrodes, for example the so called Zervas Hypophysectomy Electrode or the Gildenberg Side-Outlet electrode, as manufactured by Radionics, Inc., Burlington, Mass. However, such systems, in requiring multiple tissue punctures, increase the risk of hemorrhage, severely prolong the time of surgery and increase the level of delicacy. Also, an umbrella of off-axis lesions may not produce a desired homogenous or uniform lesion.

SUMMARY

The present disclosure relates to ablation electrode systems used for thermosurgery procedures and the like.

According to one aspect of the present disclosure, an ablation electrode system for use with a source of electrosurgical energy to ablate tissue in a living subject is provided. The ablation electrode system includes a handle assembly; and a needle electrode assembly supported in and extending from the handle assembly. The needle electrode assembly includes an outer tube having at least a conductive distal tip, a proximal end portion supported in the handle assembly, and defining a cavity therein; and an inner tube disposed at least partially within the cavity of the outer tube and having a proximal end portion supported within the handle assembly, the inner tube defining a lumen therein.

The ablation electrode system further includes a hub assembly supported within the handle assembly and fluidly connected to the needle electrode assembly. The hub assembly includes an outer shell defining a lumen therein; and an inner manifold operatively supported in the lumen of the outer shell. The inner manifold and the outer shell are configured and dimensioned so as to define a first chamber and a second chamber therebetween. The proximal end portion of the inner tube is in fluid communication with the first chamber and the proximal end portion of the outer tube is in fluid communication with the second chamber.

The ablation electrode system further includes an electrical conduit electrically connected to the outer tube of the needle electrode assembly; a first fluid conduit fluidly connected to the first chamber; and a second fluid conduit fluidly connected to the second chamber.

According to another aspect of the present disclosure, an ablation electrode system is provided and includes a handle assembly; a needle electrode assembly supported in and extending from the handle assembly. The needle electrode assembly includes an outer tube having at least a conductive distal tip, a proximal end portion supported in the handle assembly, and defining a cavity therein; and an inner tube disposed at least partially within the cavity of the outer tube and having a proximal end portion supported within the handle assembly, the inner tube defining a lumen therein.

The ablation electrode assembly includes a hub assembly supported within the handle assembly and fluidly connected to the needle electrode assembly. The hub assembly defines a first chamber and a second chamber; wherein the proximal end portion of the inner tube is in fluid communication with the first chamber and the proximal end portion of the outer tube is in fluid communication with the second chamber.

The ablation electrode assembly includes an electrical conduit electrically connected to the outer tube of the needle electrode assembly; a first fluid conduit fluidly connected to the first chamber; and a second fluid conduit fluidly connected to the second chamber.

According to yet another aspect of the present disclosure, an ablation system for ablating tissue in a living subject is provided. The ablation system includes an ablation electrode system including a needle electrode assembly. The needle electrode assembly includes an outer tube having at least a conductive distal tip and defining a cavity therein; and an inner tube disposed at least partially within the cavity of the outer tube and defining a lumen therein.

The ablation electrode system further includes a hub assembly fluidly connected to the needle electrode assembly. The hub assembly defines a first chamber and a second chamber; wherein a proximal end portion of the inner tube is in fluid communication with the first chamber and a proximal end portion of the outer tube is in fluid communication with the second chamber.

The ablation system includes a source of electrosurgical energy; a source of fluid; an electrical conduit electrically interconnecting the outer tube of the needle electrode assembly and the source of electrosurgical energy; a first fluid conduit fluidly interconnecting the source of fluid and the first chamber; and a second fluid conduit fluidly connected to the second chamber.

The present disclosure also relates to surgical device such as, for example, ablation electrode systems used for thermosurgery procedures and the like.

According to one aspect of the present disclosure, a surgical device for performing a surgical procedure on a patient is provided and includes a handle assembly including a housing having a distal end and a proximal end; a tissue engaging member supported in and extending from the distal end of the housing of the handle assembly; at least one conduit having a first end operatively associated with the tissue engaging member and a second end extending from the housing of the handle assembly; and a strain relief member supported on the at least one conduit and connected to the housing. The strain relief member and the housing are configured to enable poly-axial movement of the strain relief member with respect to the housing.

In an embodiment, the strain relief member and the housing may be connected to one another in a ball and socket arrangement.

In another embodiment, the housing may define a substantially spherical socket and the strain relief member may include at least a complimentary substantially spherical portion configured for reception in the socket of the housing.

In yet another embodiment, the strain relief member may include an annular rib extending at least partially around a circumference thereof and dimensioned to contact a surface of the housing.

In a further embodiment, the housing may define an aperture configured to receive the strain relief member, wherein the aperture defines an annular groove formed therein, and wherein the strain relief member may include an annular apron extending from a surface thereof and configured for disposition in the annular groove formed in the aperture of the housing.

In an embodiment, the housing may define an aperture configured to receive the strain relief member, and wherein the strain relief member may include an annular apron extending from a surface thereof and configured to extend beyond the aperture.

In yet another embodiment, the housing may define an aperture configured to receive the strain relief member, wherein the aperture may define at least one axial groove formed therein, and wherein the strain relief member may include an enlarged first and second body portion interconnected by a tapered portion. The strain relief member may include at least one axially extending rib configured to selectively engage each of the at least one axial grooves formed in the aperture of the housing upon a relative rotation of the strain relief member with respect to the housing.

The tissue engaging member may include at least one needle electrode assembly. Each needle electrode assembly may include an outer tube having at least a conductive distal tip, a proximal end portion supported in the housing and defining a cavity therein; and an inner tube disposed at least partially within the cavity of the outer tube and having a proximal end portion supported within the housing, the inner tube defining a lumen therethrough. The at least one conduit may include an electrical conduit electrically connected to the outer tube of each of the at least one needle electrode assemblies; a first fluid conduit fluidly connected to the inner tube of each of the at least one needle electrode assemblies; and a second fluid conduit fluidly connected to the outer tube of each of the at least one needle electrode assemblies.

The surgical device may further include a hub assembly supported within the housing of the handle assembly and fluidly connected to the needle electrode assembly. The hub assembly may include an outer shell defining a lumen therein; and an inner manifold operatively supported in the lumen of the outer shell, the inner manifold and the outer shell being configured and dimensioned so as to define a first chamber and a second chamber therebetween. The proximal end portion of the inner tube may be in fluid communication with the first chamber and the proximal end portion of the outer tube may be in fluid communication with the second chamber, wherein the first fluid conduit is connected to the first chamber and the second fluid conduit is connected to the second chamber.

The outer tube of the needle electrode assembly may be fabricated from an electrically conductive material. A layer of insulative material may be disposed on an outer surface of the outer tube and wherein the distal tip of the outer tip may be exposed. The inner tube may deliver fluid to the distal tip of the outer tube.

The surgical device may further include a thermocouple assembly electrically connected to the inner tube. The thermocouple assembly may include a constantan wire extending through the lumen of the inner tube and electrically connected to a distal end of the inner tube.

The inner manifold may define a lumen therein interconnecting the second chamber of the hub assembly to the second fluid conduit.

An adhesive may be applied to a proximal end of the inner manifold and the outer shell to at least one to secure the inner manifold within the outer shell and to seal the hub assembly from fluid leaks from between the outer shell and the inner manifold. A seal element may be provided between the outer shell and the inner manifold of the hub assembly to prevent transmission of fluid between the first chamber and the second chamber.

The surgical device may further include a plurality of needle electrode assemblies supported in and extending from the handle assembly. A proximal end portion of each inner tube may be in fluid communication with the first chamber and a proximal end portion of each outer tube may be in fluid communication with the second chamber.

According to another aspect of the present disclosure, an ablation electrode system for use with a source of electrosurgical energy to ablate tissue in a living subject is provided. The ablation electrode system includes a handle assembly including a housing; and at least one needle electrode assembly supported in and extending from the housing of the handle assembly. Each needle electrode assembly includes an outer tube having at least a conductive distal tip, a proximal end portion supported in the housing of the handle assembly, and defining a cavity therein; and an inner tube disposed at least partially within the cavity of the outer tube and having a proximal end portion supported within the housing of the handle assembly, the inner tube defining a lumen therein. The ablation electrode system further includes an electrical conduit electrically connected to the outer tube of each of the at least one needle electrode assemblies; a first fluid conduit fluidly connected to the inner tube of each of the at least one needle electrode assemblies; a second fluid conduit fluidly connected to the outer tube of each of the at least one needle electrode assemblies; and a strain relief member connected to the housing and having each of the conduits extending therethrough. The strain relief member and the housing are configured to enable poly-axial movement of the strain relief member with respect to the housing.

For a better understanding of the present invention and to show how it may be carried into effect, reference will be made by way of example to the accompanying drawings.

BRIEF DESCRIPTION OF THE DRAWINGS

In the drawings, which constitute a part of the specification, exemplary embodiments exhibiting various objectives and features hereof are set forth, specifically:

FIG. 9 is a longitudinal cross-sectional view of the ablation electrode system of FIG. 8;

FIG. 10 is a longitudinal cross-sectional view of the outer shell of the hub assembly of FIG. 9, including needle electrodes shown operative connected thereto;

FIG. 10A is a distal end view of the outer shell of the hub assembly of the ablation electrode system of FIG. 8;

DETAILED DESCRIPTION OF EMBODIMENTS

Figure 1:
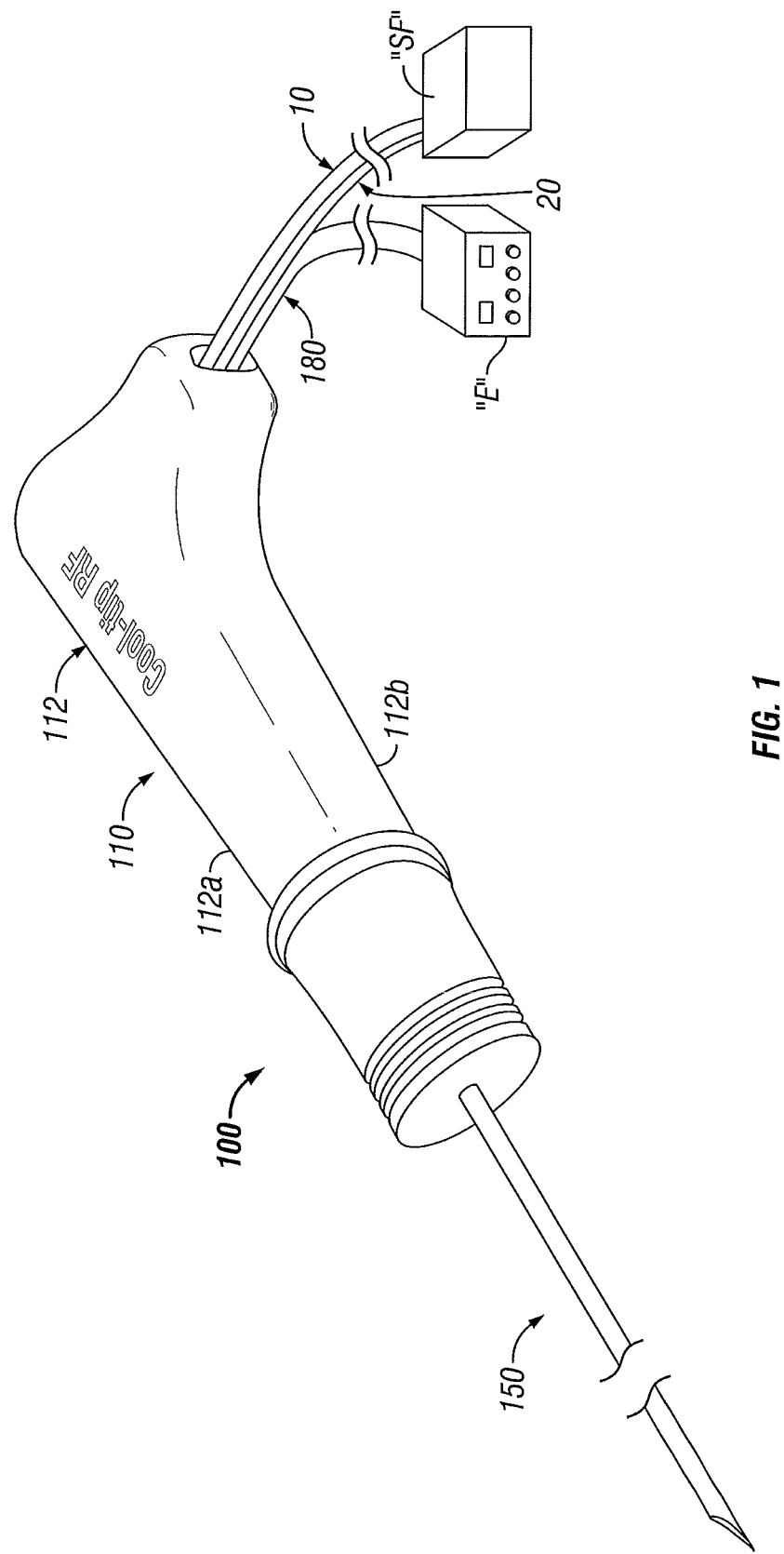
FIG. 1 is a perspective view of an ablation electrode system in accordance with an embodiment of the present disclosure.

Embodiments of ablation electrode systems, in accordance with the present disclosure, will now be described in detail with reference to the drawings figures wherein like reference numerals identify similar or identical structural elements. As shown in the drawings and described throughout the following description, as is traditional when referring to relative positioning on a surgical instrument, device or apparatus, the term "proximal" refers to the end of the instrument, apparatus or device that is closer to the user and the term "distal" refers to the end of the apparatus that is further away from the user.

Referring initially to FIGS. 1-7, an electrode ablation system, according to an embodiment of the present disclosure, is generally designated as ablation system 100. Ablation system 100 includes a housing or handle assembly 110, and at least one needle electrode assembly 150 supported within and extending from housing assembly 110. Housing assembly 110 and needle electrode assembly 150 define a central longitudinal axis "X".

Figure 2:
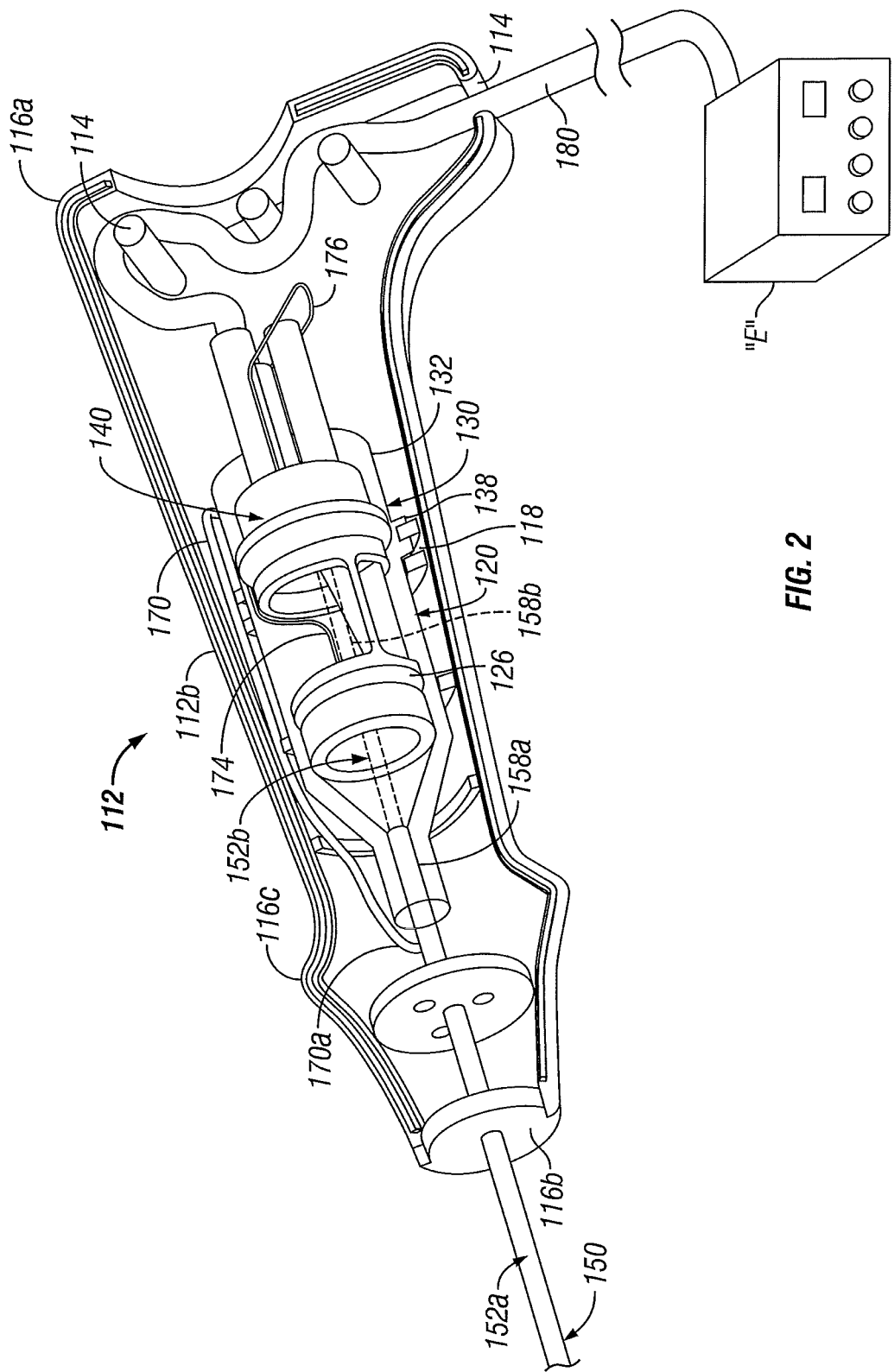
FIG. 2 is an enlarged perspective view of the ablation electrode system of FIG. 1, with a handle half-section removed therefrom and a hub assembly disposed therein shown partially broken away.
Figure 3:
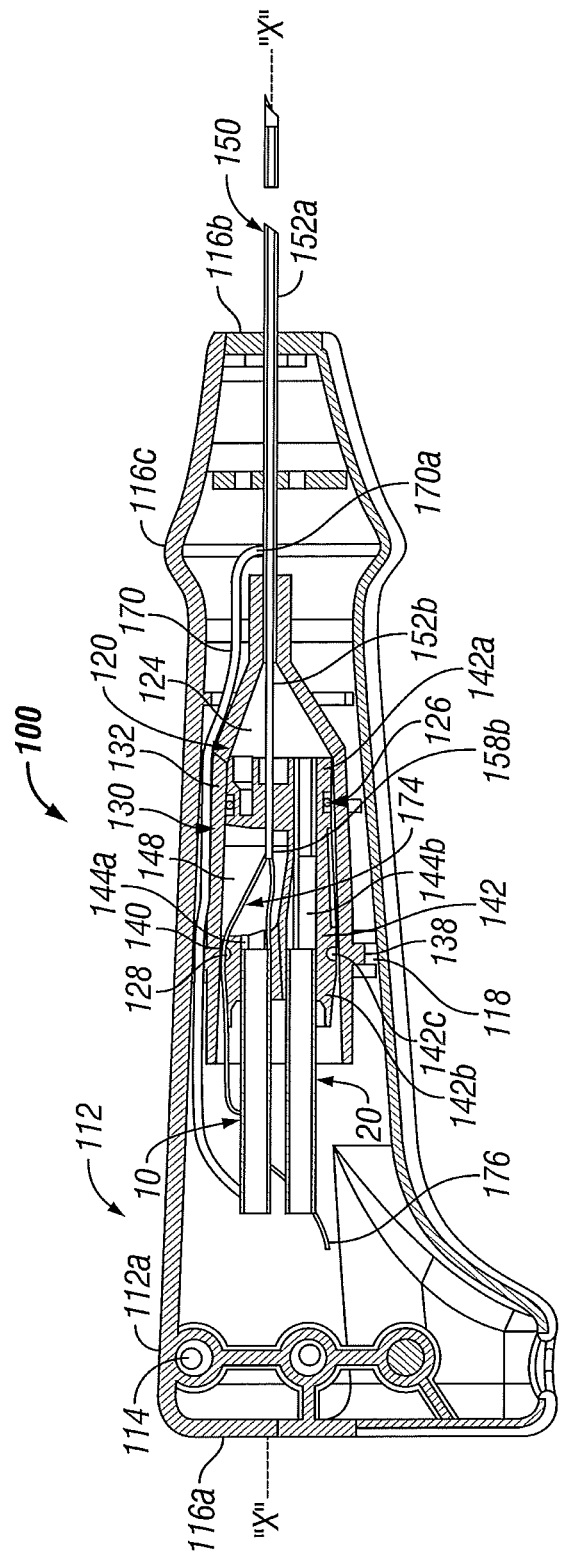
FIG. 3 is a longitudinal cross-sectional view of the ablation electrode system of FIGS. 1 and 2.

As seen in FIGS. 1-3, housing assembly 110 includes a housing or handle 112 having first half-section 112a and a second half-section 112b selectively connectable to one another (e.g., in a snap-fit manner) via connecting structure 114 or the like. In one embodiment, housing 112 has a substantially conical shape defining a flattened proximal surface 116a and a flattened distal surface 116b (FIGS. 2 and 3). Housing 112 further includes an annular ramp-like structure 116c extending from the surface thereof. Ramp-like structure 116c acts as a surface against which an operators fingers contact for distal advancement of needle electrode 150 into the patient and/or proximal withdrawal of needle electrode 150 from the patient.

As seen in FIGS. 2-8, electrode ablation system 100 further includes a hub assembly 120 supported in housing 112 of housing assembly 110. Hub assembly includes a hub assembly outer shell 130 and a hub assembly inner manifold 140 disposed within outer shell 130. Outer shell 130 and inner manifold 140 of hub assembly are each fabricated from a suitable electrically non-conductive material.

As seen in FIGS. 2-5, hub assembly outer shell 130 includes a body portion 132 defining a central lumen 134 extending therethrough. Outer shell 130 defines a central longitudinal axis "X1" extending through central lumen 134. In an embodiment, when outer shell 130 is positioned in housing 112, the central longitudinal "X1" axis thereof at least substantially aligns with the central longitudinal "X" axis of housing 112 and needle electrode assembly 150. Central lumen 134 of outer shell 130 includes a tapered distal end 136 defining a constricted passage 134a therethrough. Passage 134a is sized to support and receive needle electrode assembly 150 therein.

Body portion 132 of outer shell 130 may include an annular flange 138 formed therearound. As seen in FIGS. 2 and 3, annular flange 138 of outer shell 130 is receivable in a complementary annular channel or groove 118 formed or provided in housing 112. Accordingly, annular flange 138 and annular groove 118 cooperate to fix the location of hub assembly 120 relative to housing 112.

As seen in FIGS. 2-4, 6 and 7, inner manifold 140 is configured and dimensioned for support within lumen 134 of outer shell 130. Inner manifold 140 includes a body portion 142 defining a first or inflow lumen 144a formed at least partially in a proximal end portion 142b thereof. Inner manifold 140 further includes a second or outflow lumen 144b extending entirely therethrough. Inner manifold 140 further includes a third lumen 144c formed at least partially in a distal end portion 142a thereof.

Figure 4:
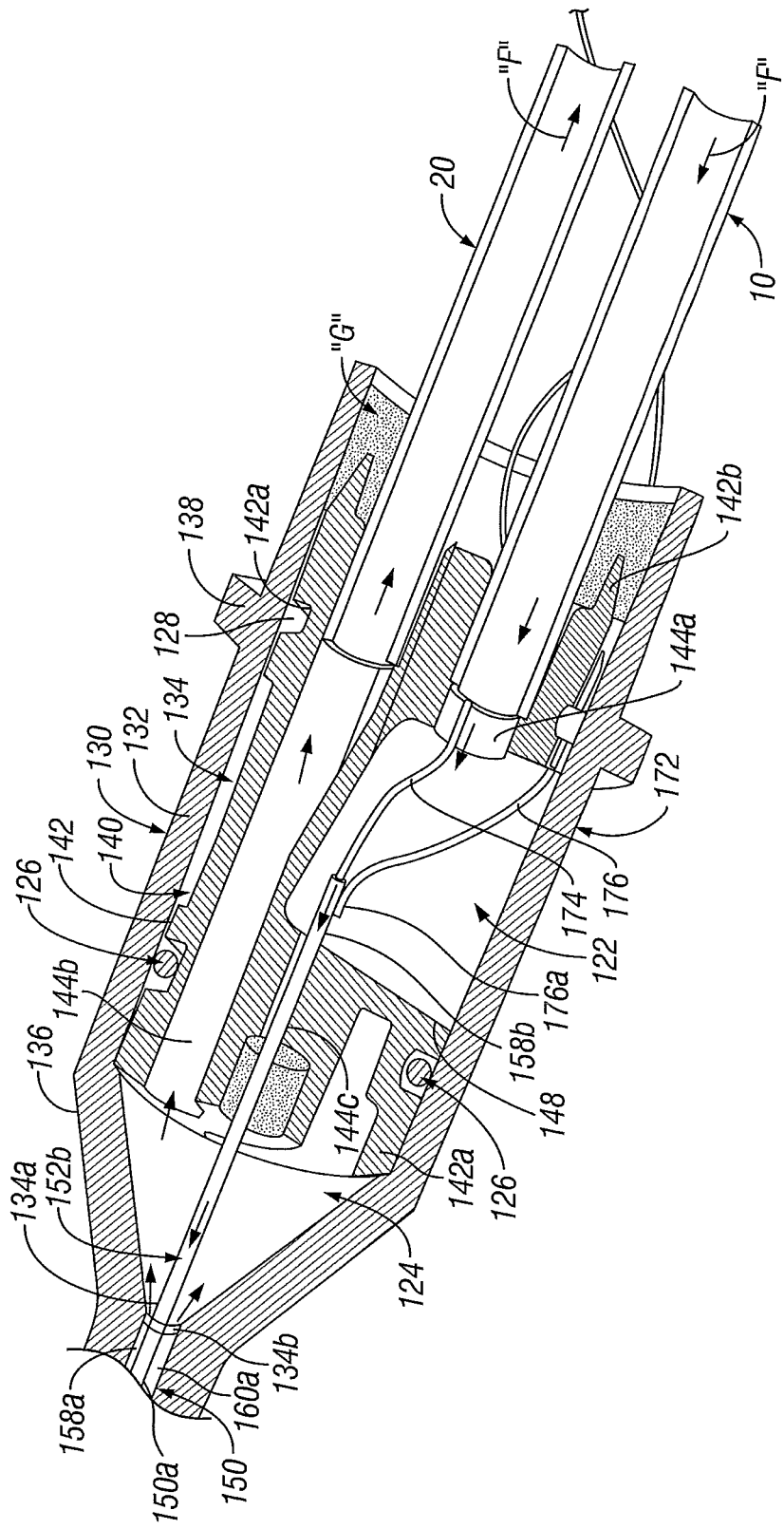
FIG. 4 is an enlarged longitudinal cross-sectional view of the hub assembly of FIGS. 2 and 3.

As seen in FIGS. 3, 4, 6 and 7, inner manifold 140 defines a first recess 148 formed therein such that when inner manifold 140 is inserted into lumen 134 of outer shell 130, first recess 148 defines a first cavity or chamber 122 between outer shell 130 and inner manifold 140. As seen in FIGS. 3 and 4, first lumen 144a and third lumen 144c are each in fluid communication with first chamber 122.

With continued reference to FIGS. 3 and 4, when inner manifold 140 is inserted into lumen 134 of outer shell 130, a second chamber 124 is defined in tapered distal end 136 of outer shell 130. When inner manifold 140 is so positioned, second lumen 144b of manifold 140 is in fluid communication with the second chamber 124.

As seen in FIGS. 3, 4, 6 and 7, body portion 142 of inner manifold 140 may include an annular groove 142a formed therein. As seen in FIGS. 3 and 4, annular groove 142a of body portion 142 of inner manifold 140 is configured and dimensioned to receive a complementary annular flange or rib 128 formed in body portion 132 of outer shell 130. Accordingly, annular flange 128 and annular groove 142c cooperate to fix the location of inner manifold 140 relative to outer shell 130.

In addition, as seen in FIG. 4, a glue "G," including and not limited to, adhesives, epoxies, bonding agents, cements, silicones, and the like, is applied in a proximal or rear portion of lumen 134 of outer shell 130, on a proximal or rear surface of inner manifold 140, and at locations therebetween. Glue "G" functions to further secure inner manifold 140 within outer shell 130 and to create a seal between outer shell 130 and inner manifold 140 to thereby inhibit and/or prevent the escape of fluid from therebetween.

In an embodiment, as seen in FIGS. 2-4, hub assembly 120 includes a seal element 126 (e.g., an O-ring) disposed between body portion 132 of outer shell 130 and body portion 142 of inner manifold 140. Seal element 126 functions to reduce and/or prevent fluid from traveling between first chamber 122 and second chamber 124.

As seen in FIGS. 1-4, a first or in-flow conduit 10 is fluidly connected to first lumen 144a of inner manifold 140. A distal end of first conduit 10 extends through housing 112 of housing assembly 110 and is frictionally inserted into first lumen 144a of inner manifold 140 of hub assembly 120.

With continued reference to FIGS. 1-4, a second or out-flow conduit 20 is fluidly connected to second lumen 144b of inner manifold 140. Desirably, a distal end of second conduit 20 extends through housing 112 of housing assembly 110 and is frictionally inserted into second lumen 144b of inner manifold 140 of hub assembly 120.

Figure 5:
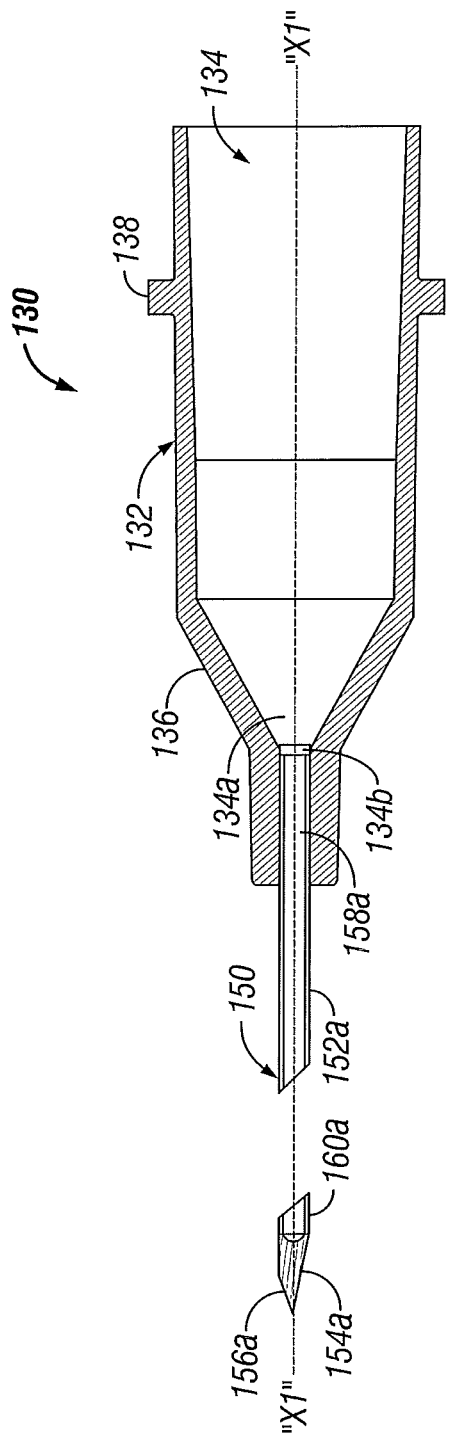
FIG. 5 is a longitudinal cross-sectional view of the outer shell of the hub assembly of FIGS. 2-4, including a needle electrode shown operative connected thereto.
Figure 6:
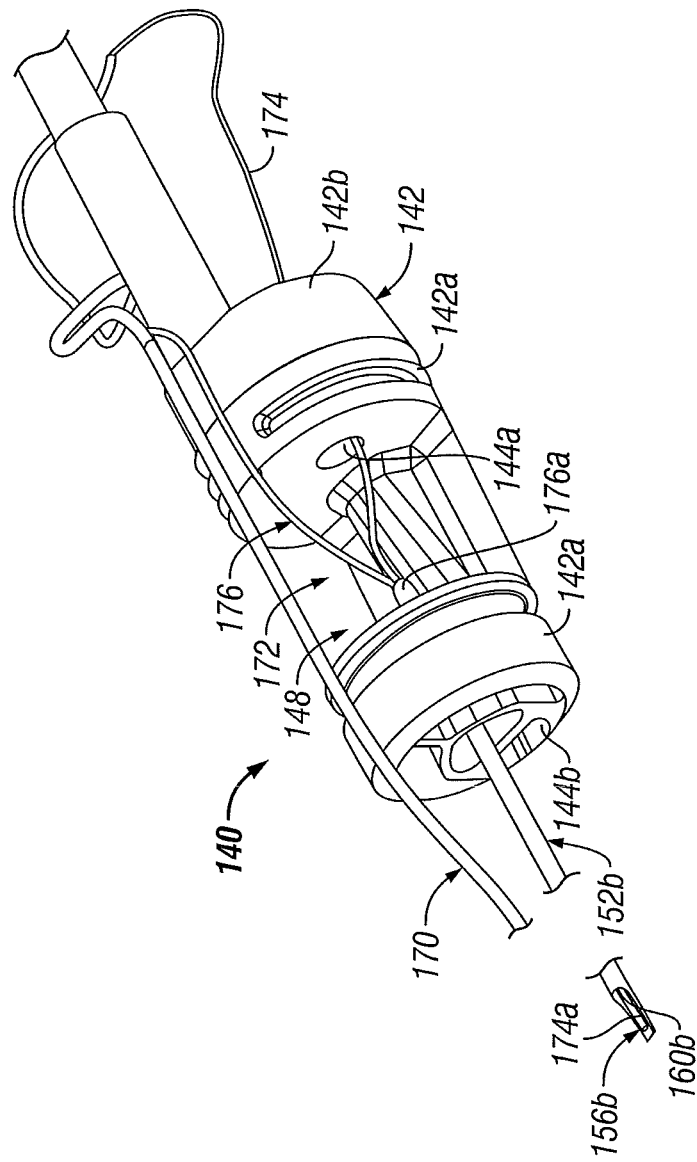
FIG. 6 is a perspective view an inner manifold of the hub assembly of FIGS. 2-4.

Turning now to FIGS. 1-5, needle electrode assembly 150 is described in greater detail. Needle electrode assembly 150 includes an outer tube 152a having an exposed distal end portion 154a terminating in a sharpened distal tip 156a which is constructed so as to penetrate tissue with a minimum risk of hemorrhage from the puncture tract. Outer tube 152a is constructed from a suitable electrically conductive material. Outer tube 152a includes a proximal end portion 158a supported in housing 112, and in an embodiment, in a distal lumen 134b formed in and extending distally from constricted passage 134a of outer shell 130, as seen in FIGS. 4 and 5. Outer tube 152a is hollow and defines a cavity 160a therein.

In an embodiment, the non-exposed part of outer tube 152a may be surrounded by an insulating material. The insulating material may be any material which is biologically acceptable and suitable for insertion into tissue. Since distal end portion 154a is exposed or non-insulated, distal end portion 154a is capable of DC or AC delivery, preferably RF delivery.

Needle electrode assembly 150 further includes an inner tube 152b disposed substantially co-axially within cavity 160a of outer tube 152a. Inner tube 152b includes a distal end portion 156b (see FIGS. 6 and 7) located near distal end portion 154a of outer tube 152a and a proximal end portion 158b extending from proximal end portion 158a of outer tube 152a. Proximal end portion 158b of inner tube 152b extends through constricted passage 134a and into or through third lumen 144c of inner manifold 140. It is envisioned that proximal end portion 158b of inner tube 152b is in fluid communication with first cavity or chamber 122 defined between inner manifold 140 and outer shell 130, see FIGS. 2-4.

In use, cooling fluid "F" is delivered to distal tip 156a of outer tube 152a from in-flow conduit 10. In particular, cooling fluid "F" travels from in-flow conduit 10, into first chamber 122, into lumen 160b (see FIGS. 6 and 7) of inner tube 152b of needle electrode assembly 150, to distal tip 156a of outer tube 152a. Cooling fluid "F" is led away from distal tip 156a of outer tube 152a through cavity 160a, through second chamber 124, through second lumen 144b of inner manifold 140, and out through out-flow tube 20. Cooling fluid "F" may be communicated to a collecting container (not shown) or back to a source of fluid "SF" (see FIG. 1) for re-circulation. Circulation of cooling fluid "F" may be established with the use of a suitable pump (not explicitly shown).

As seen in FIGS. 2, 3, 6 and 7, electrode ablation system 100 further includes a first electrical conduit 170 extending through housing 112 and electrically connected to outer tube 152a of needle electrode assembly 150. In particular, first electrical conduit 170 includes a distal end 170a electrically connected to outer tube 152a at a location distal of hub assembly 120 and within housing 112. First electrical conduit 170 is also electrically connected to a source of electrosurgical energy "E". Accordingly, electrosurgical energy may be delivered from the source of electrosurgical energy, through first electrical conduit 170, to outer tube 152a.

As seen in FIGS. 2-4, 6 and 7, electrode ablation system 100 further includes a thermocouple assembly 172 operatively associated with inner tube 152b. Thermocouple assembly 172 includes a first wire or thermocouple 174 extending through lumen 160b of inner tube 152b. A distal end 174a of first wire 174 is desirably electrically secured to distal end portion 156b of inner tube 152b, as by, for example, soldering and the like. First wire 174 may be fabricated from constantan (i.e., a high-resistance alloy of approximately 40% nickel and 60% copper). However, other suitable materials may be used for first wire 174, such as, for example, any suitable conductor that is dissimilar from inner tube 152b (e.g., stainless steel) such that a thermocouple is created between the two materials.

Thermocouple assembly 172 further includes a second wire 176 having a distal end 176a electrically connected to inner tube 152b. In an embodiment, distal end 176a of second wire 176 is connected to a proximal end portion 158b of inner tube 152b. Second wire 176 functions to electrically interconnect first wire 174 and a thermocouple measuring circuit. Accordingly, a temperature measurement signal from the thermocouple measuring circuit may then be sent to an electrosurgical energy source "E", and/or a central processing unit for monitoring.

Figure 7:
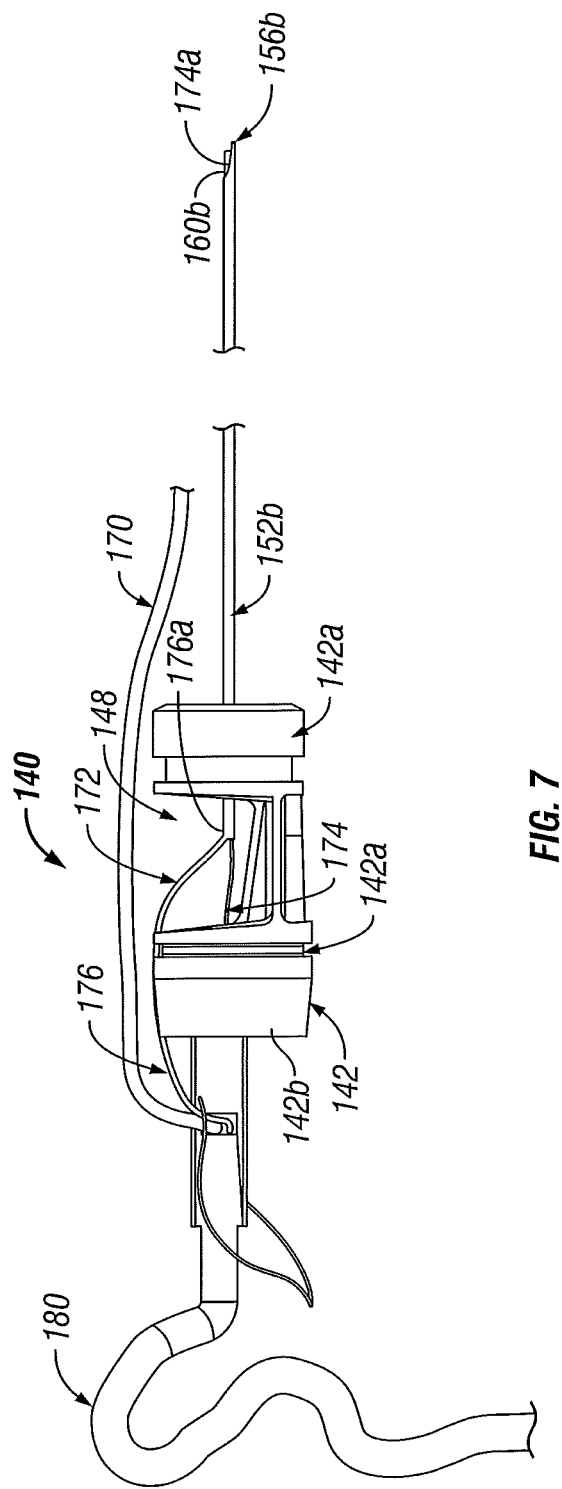
FIG. 7 is a longitudinal cross-sectional view of the inner manifold of FIG. 6.
Figure 8:
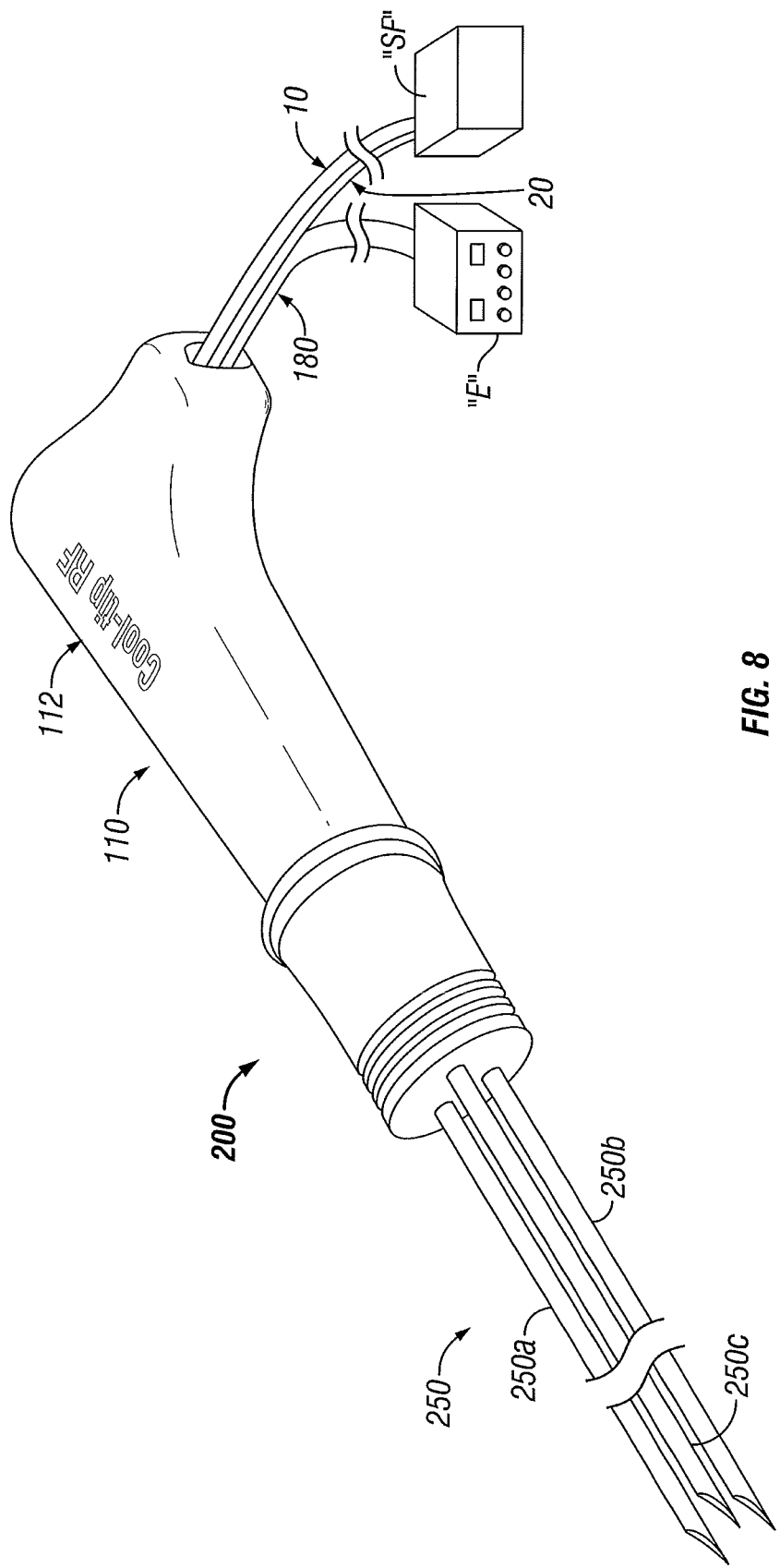
FIG. 8 is a perspective view of an ablation electrode system according to an alternate embodiment of the present disclosure.

As seen in FIGS. 1, 2 and 7, each of electrical conduit 170, first wire 174 and second wire 176 may be contained in a single cable 180.

Turning now to FIGS. 8-12, an electrode ablation system, in accordance with another embodiment of the present disclosure, is generally designated as 200. Electrode ablation system 200 is substantially similar to ablation system 100 and will be discussed in detail to the extent necessary to identify differences in construction and operation. Unlike electrode ablation system 100 which includes a single needle electrode assembly 150, electrode ablation system 200 includes three needle electrode assemblies 250a-250c extending distally from housing 112 of housing assembly 110. While a single and three needle electrode assemblies have been shown and described herein, any suitable number of needle electrode assemblies may be provided.

As seen in FIGS. 9-12, hub assembly 220 of electrode ablation system 200 includes a hub assembly outer shell 130 and a hub assembly inner manifold 240 operatively disposed within outer shell 230.

As seen in FIGS. 9, 10 and 10A, hub assembly outer shell 230 includes a body portion 232 defining a central lumen 234 extending therethrough. Desirably, outer shell 230 includes three constricted passages 236a-236c extending through a distal end portion 230a of outer shell 230 and in fluid communication with central lumen 234. Desirably, each passage 236a-236c is sized to support and receive a proximal end of outer tube 252a of a respective needle electrode assembly 250a-250c.

Figure 11:
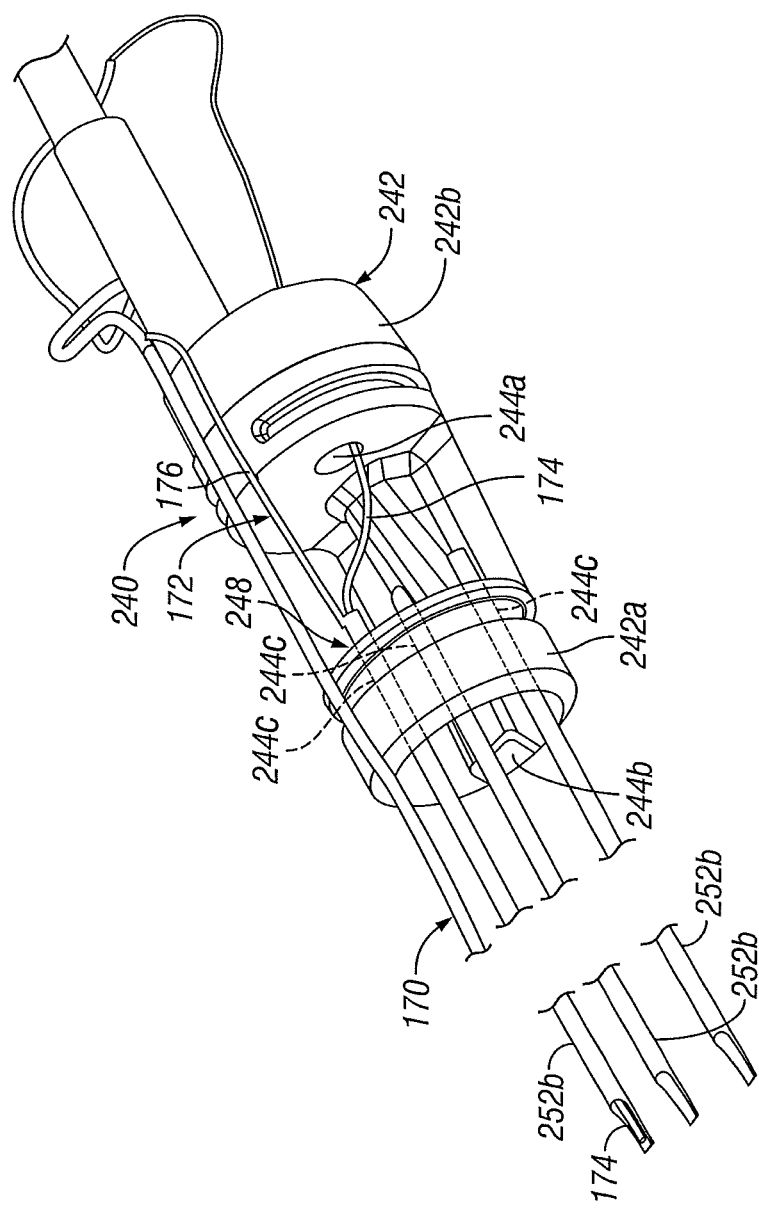
FIG. 11 is a perspective view an inner manifold of the hub assembly of FIG. 9.
Figure 12:
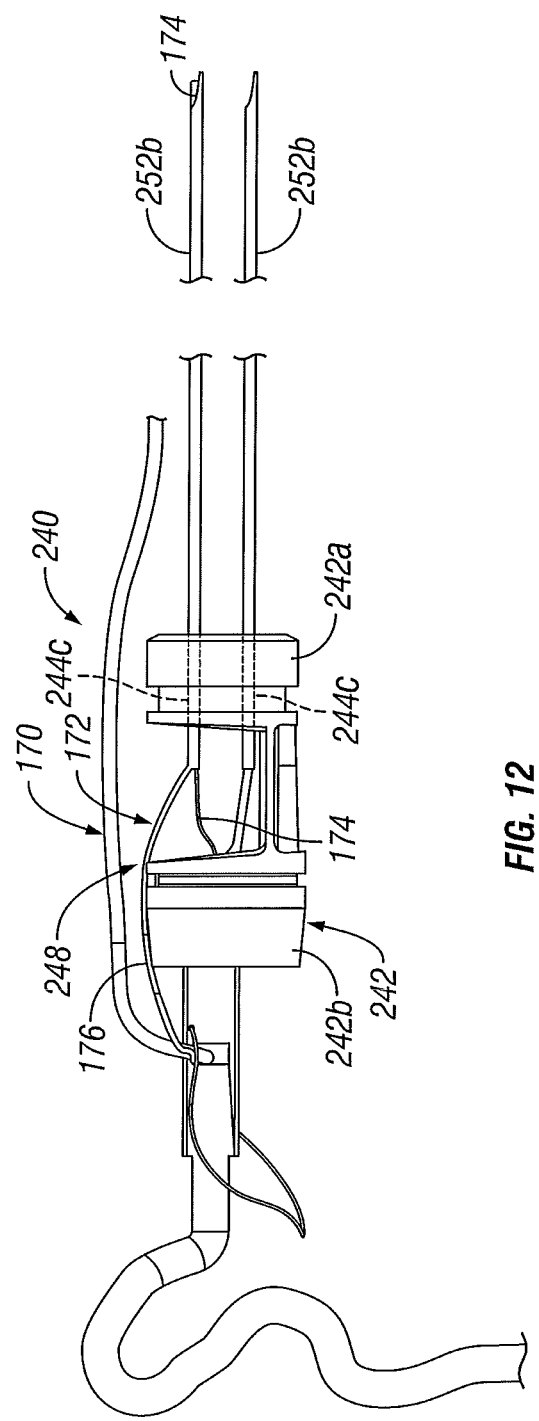
FIG. 12 is a longitudinal cross-sectional view of the inner manifold of FIG. 11.
Figure 13:
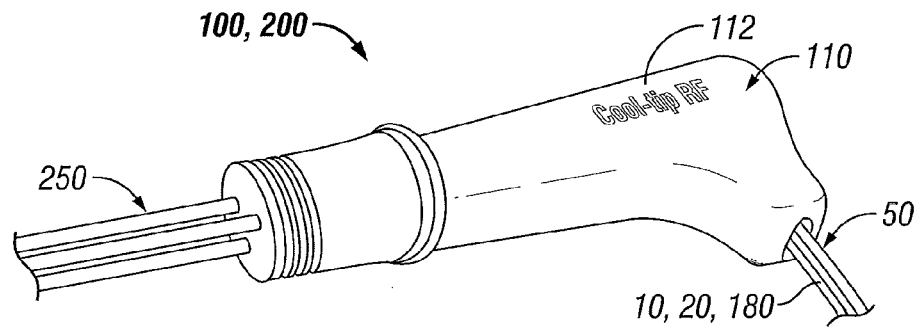
FIG. 13 is a perspective view of an ablation electrode system illustrating a strain relief member operatively associated therewith for support of the cables and/or conduits entering the handle.

As seen in FIGS. 9, 11 and 12, inner manifold 240 is configured and dimensioned for support within lumen 234 of outer shell 230. Inner manifold 240 includes a body portion 242 defining a first or inflow lumen 244a formed at least partially in a proximal end portion 242b thereof. Inner manifold 240 further includes a second or outflow lumen 244b extending entirely therethrough. Inner manifold 240 further includes a plurality of third lumens 244c formed at least partially in a distal end portion thereof 242a. Each third lumen 244c of inner manifold 240 is configured and dimensioned to receive and support a proximal end of a respective inner tube 252b of needle electrode assemblies 250a-250c therein.

As seen in FIGS. 9, 11 and 12, inner manifold 240 defines a first recess 248 formed therein such that when inner manifold 240 is inserted into lumen 234 of outer shell 230, first recess 248 defines a first cavity or chamber 222 between outer shell 230 and inner manifold 240. As can be appreciated and similar to hub assembly 120 of electrode ablation system 100, first lumen 244a and each third lumen 244c are in fluid communication with first chamber 222.

With continued reference to FIGS. 9, 11 and 12, when inner manifold 240 is inserted into lumen 234 of outer shell 230, a second chamber 224 is defined in distal end portion 236 of lumen 234 of outer shell 230. When inner manifold 240 is so positioned, second lumen 244b of manifold 240 is in fluid communication with the second chamber 224.

As seen in FIGS. 9-12, each needle electrode assembly 250a-250c of electrode ablation system 200 is substantially similar to needle electrode assembly 150 of electrode ablation system 100, and therefore reference may be made to the detailed discussion of needle electrode assembly 150 for an understanding and description of needle electrode assemblies 250a-250c.

Use of electrode ablation system 200 will now be described in detail. In use, cooling fluid "F" is delivered to a distal tip 256 of each outer tube 252a. In particular, cooling fluid travels from in-flow conduit 10, into first chamber 222, into a lumen of an inner tube (see FIGS. 6 and 7) of each needle electrode assembly 250a-250c, to a distal tip 256 of the outer tube of each needle electrode assembly 250a-250c. The cooling fluid is led away from distal tip 256 of the outer tube of each needle electrode assembly 250a-250c, through second chamber 224, through second lumen 244b of inner manifold 240, and out through out-flow tube 20.

As seen in FIGS. 11 and 12, a first wire 174 of thermocouple assembly 172 extends through lumen 160b (see FIG. 6) of at least one inner tube 252b of needle electrode assemblies 250a-250c. As mentioned above, a distal end 174a of first wire 174 is desirably electrically secured to a distal end portion of inner tube 252b, as by, for example, soldering and the like. Desirably, first wire 174 is fabricated from constantan or the like (i.e., a high-resistance alloy of approximately 40% nickel and 60% copper). A second wire 176 of thermocouple assembly 172 has a distal end electrically connected to inner tube 252b The handle of needle electrode system 200 is configured and adapted so as to maintain needle electrode assemblies 250a-250c substantially parallel to one another during insertion and/or placement of needle electrode assemblies 250a-250c into a target surgical site.

Turning now to FIGS. 13-18, electrode ablation systems 100, 200 may each include an adjustable cord strain relief member 50 operatively disposed on cable 180, in-flow conduit 10, and/or out-flow conduit 20. Strain relief member 50 is configured and dimensioned for operative engagement in an aperture 114 (see FIGS. 1 and 2) of housing 112 of handle assembly 110. In an embodiment, aperture 114 is formed in a side of housing 112 of handle assembly 110 such that cable 180, in-flow conduit 10 and/or out-flow conduit 20 may extend out of the side thereof. By having cable 180, in-flow conduit 10 and/or out-flow conduit 20 exit from a side of housing 112 of handle assembly 110 a strain relief for cable 180, in-flow conduit 10 and/or out-flow conduit 20 is established.

Strain relief member 50 includes a body portion 52 having a substantially hour-glass configuration. Body portion 52 may include a first substantially spherical portion 52a and a second substantially spherical portion 52b. Desirably, second portion 52b of body portion 52 is poly-axially supported (e.g., in the manner of a ball and socket joint) within a complementarily sized and shaped aperture 114.

Figure 14:
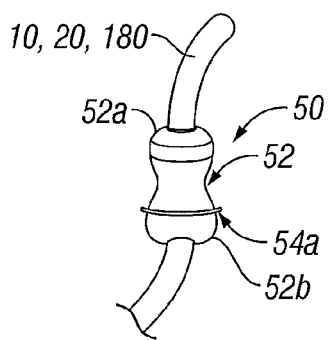
FIG. 14 is a schematic perspective view of a strain relief member for use with ablation electrode system.
Figure 15:
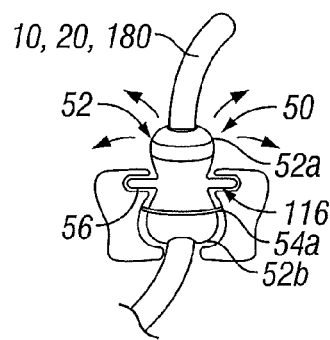
FIG. 15 is a schematic longitudinal cross-sectional view of another strain relief member shown supported in the handle of the ablation electrode system.
Figure 16:
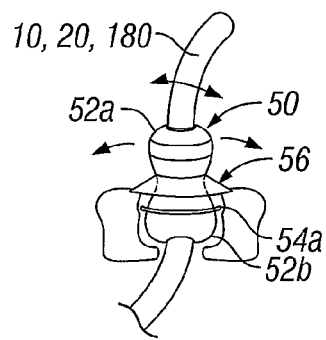
FIG. 16 is a schematic longitudinal cross-sectional view of yet another strain relief member shown supported in the handle of the ablation electrode system.

As seen in FIGS. 14-16, an annular rib 54a may be provided on the surface of second body portion 52a for engaging the inner surface of shaped aperture 114. Strain relief member 50 may also be provided with a shield or apron 56 extending radially therefrom. Shield 56 may be disposed within an appropriately sized recess 116 formed in handle 112, as seen in FIG. 15, or may be disposed externally of handle 112, as seen in FIG. 16.

Figure 17:
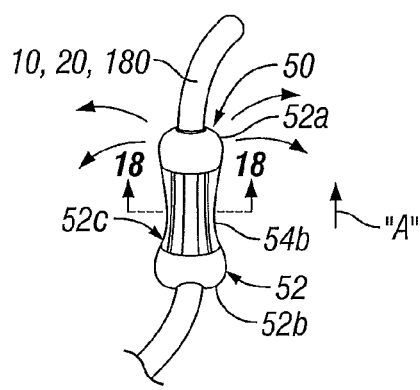
FIG. 17 is a schematic perspective view of another strain relief member for use with ablation electrode system.
Figure 18:
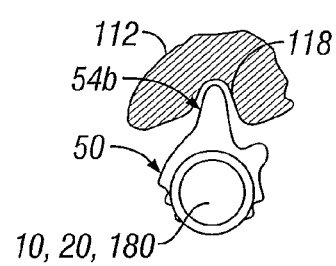
FIG. 18 is a cross-sectional view of the strain relief member of FIG. 17, as taken through 18-18 of FIG. 17.

As seen in FIGS. 17 and 18, strain relief member 50 may include means for locking including a tapered portion 52c disposed between first body portion 52a and second body portion 52b, and at least one longitudinally oriented locking rib 54*b* projecting from tapered portion 52*c*. Locking rib 54*b* is configured and dimensioned to selectively engage complementary channels 118 formed in handle 112. In use, as strain relief member 50 is moved in a first direction (as indicated by arrow "A"), locking rib 54*b* disengages channels 118 to unlock strain relief member 50, and as strain relief member 50 is moved in a second direction (opposite to direction "A"), locking rib 54*b* engages channels 118 to lock strain relief member 50.

The foregoing description is merely a disclosure of particular embodiments and is no way intended to limit the scope of the invention. Other possible modifications are apparent to those skilled in the art and all modifications are to be defined by the following claims.

What is claimed is:

1. An electrosurgical instrument, comprising:
    a handle assembly including a housing having a distal end and a proximal end, an outer shell, and a manifold insertable into the outer shell, such that upon insertion, the manifold defines a first chamber and a second chamber within the handle assembly, the second chamber disposed distal of the first chamber, the manifold including a first opening and a second opening, the first opening and the second opening defined on a proximal portion of the manifold;
    a first tube inserted into the first opening;
    a second tube inserted into the second opening;
    a tissue engaging member coupled to the distal end of the housing;
    an inner tube having a proximal portion disposed within the handle assembly and a distal portion coaxially disposed within the tissue engaging member, wherein inner tube is in direct fluid communication with the first chamber and the tissue engaging member is in fluid communication with the second chamber; and
    a thermocouple assembly including a first thermocouple coupled to a proximal end of the inner tube within the handle assembly and a second thermocouple coupled to a distal end of the inner tube.

2. The surgical instrument according to claim 1, wherein the first tube is fluidly coupled to the first chamber, the second tube is fluidly coupled to the second chamber, and the first tube and the second tube are configured to couple to a recirculating source of fluid.

3. The surgical instrument according to claim 1, wherein the second thermocouple extends through a lumen of the inner tube.

4. The surgical instrument according to claim 1, wherein the first thermocouple includes constantan.

5. The surgical instrument according to claim 1, wherein at least one of the first tube or the second tube is coupled to the housing by a strain relief member movable with respect to the housing.

6. The surgical instrument according to claim 5, wherein the strain relief member is disposed within the housing.

7. The surgical instrument according to claim 5, wherein the strain relief member includes an annular rib extending into a portion of the housing.

8. An electrosurgical system, comprising:
    an electrosurgical instrument, including:
        a handle assembly including a housing having a distal end and a proximal end, an outer shell, and a manifold insertable into the outer shell, such that upon insertion, the manifold defines a first chamber and a second chamber within the handle assembly, the second chamber disposed distal of the first chamber, the manifold including a first opening and a second opening, the first opening and the second opening defined on a proximal portion of the manifold;
        a first tube inserted into the first opening;
        a second tube inserted into the second opening;
        a tissue engaging member coupled to the distal end of the housing;
        an inner tube having a proximal portion disposed within the handle assembly and a distal portion coaxially disposed within the tissue engaging member, wherein inner tube is in direct fluid communication with the first chamber and the tissue engaging member is in fluid communication with the second chamber; and
        a thermocouple assembly including a first thermocouple coupled to a proximal end of the inner tube within the handle assembly and a second thermocouple coupled to a distal end of the inner tube;
    a source of treatment energy coupled to the tissue engaging member; and
    a source of fluid coupled to the tissue engaging member and the inner tube.

9. The surgical system according to claim 8, wherein the first tube is fluidly coupled to the first chamber, the second tube is fluidly coupled to the second chamber, and the first tube and the second tube are configured to couple to the source of fluid.

10. The surgical system according to claim 8, wherein the second thermocouple extends through a lumen of the inner tube.

11. The surgical system according to claim 8, wherein the first thermocouple includes constantan.

12. The surgical system according to claim 8, wherein at least one of the first tube or the second tube is coupled to the housing by a strain relief member movable with respect to the housing.

13. The surgical system according to claim 12, wherein the strain relief member is disposed within the housing.

14. The surgical system according to claim 12, wherein the strain relief member includes an annular rib extending into a portion of the housing.

* * * * *